United States Patent [19]

Shimomura

[11] Patent Number: 5,926,124
[45] Date of Patent: Jul. 20, 1999

[54] SIGNAL PROCESSOR FOR A MEASUREMENT APPARATUS

[75] Inventor: Manabu Shimomura, Nishikyo-ku, Japan

[73] Assignee: Shimadzu Corporation, Kyoto, Japan

[21] Appl. No.: 08/888,243

[22] Filed: Jul. 3, 1997

[30] Foreign Application Priority Data

Jul. 5, 1996 [JP] Japan .................................. 8-195761

[51] Int. Cl.$^6$ ................................................ G01N 30/86
[52] U.S. Cl. .......................................... 341/139; 341/155
[58] Field of Search ................................ 341/120, 118, 341/155, 139, 161

[56] References Cited

U.S. PATENT DOCUMENTS 4,842,085   6/1989   Lang .......................................... 177/164
4,859,964   8/1989   Jorgensen .................................. 330/279

*Primary Examiner*—Marc S. Hoff
*Assistant Examiner*—Peguy JeanPierre
*Attorney, Agent, or Firm*—Armstrong, Westerman, Hattori, McLeland & Naughton

[57] ABSTRACT

In a signal processor according to the present invention, an analog output signal of a measurement apparatus is first amplified by an amplifier, where the gain can be changed. The amplified analog signal is then sampled and converted by an A/D converter to a digital data. When the value of the digital data is smaller than a preset reference value, a gain determining element determines the gain at a larger value, which will be used for the next sampled data. When, conversely, the value of the digital data is larger than another preset reference value, the gain determining element determines the gain at a smaller value so that a signal saturation in the A/D converter will be prevented in the next data sampling. When the value of one of two consecutively sampled digital data is greater than the preset second reference value, the data is disregarded and the other data is used as the measurement data, which prevents producing an erroneous measurement data output and assures the quality and preciseness of the sample analysis using the measurement data.

5 Claims, 3 Drawing Sheets

SIGNAL PROCESSOR FOR A MEASUREMENT APPARATUS

The present invention relates to a signal processor used in a measurement apparatus or sample analyzer such as a gas-chromatograph/mass-spectrometer (GC/MS), especially to those parts relating to converting an analog signal from the measurement apparatus into digital data.

BACKGROUND OF THE INVENTION

In a signal processor of a measurement apparatus or sample analyzer such as a GC/MS, the analog output signal from the detector is converted to digital data by an A/D converter, and the data is stored once in a memory. The data is then read out from the memory, and various calculations are performed with the data to analyze the sample from various aspects.

In order to analyze the sample precisely, it is necessary to obtain data having a large dynamic range. Since the dynamic range of the data obtained by such a method as described above is limited by the dynamic range of the A/D converter, following measures are taken to expand the dynamic range of the data obtained.

FIG. 5 shows a data sampling section of a conventional signal processor. An analog output signal from a detector of a sample analyzer (not shown) is introduced into two paths. On one path are provided a first pre-amplifier 10, a first sample holding (S/H) circuit 11 and a first analog switch 12, and on the other path are provided a second pre-amplifier 13, a second sample holding (S/H) circuit 14 and a second analog switch 15. The first pre-amplifier 10 has an amplifying gain of unity, and the second pre-amplifier has an amplifying gain of sixty-four (64). The signals passing through the two paths join to enter a third sample holding (S/H) circuit 16, where the joined analog signal is held, and the held signal is converted to digital data by an A/D converter 17. The digital data is given to a microcomputer ($\mu$COM) 20 and stored in a memory (not shown). The first, second and third S/H circuits 11, 14, 16, the first and second analog switches 12, 15 and the A/D converter 17 receive clock pulse signals from a clock pulse generator 19 which is controlled by a timing control signal SP from the microcomputer 20. The output of the second S/H circuit 14 is also given to a comparator 18, where the output is compared with a preset reference signal and the comparison result is given to the clock pulse generator 19.

The operation of the data sampling section of FIG. 5 is as follows. The output signal of the detector is amplified by the first pre-amplifier 10 and the second pre-amplifier 13 respectively, and is held by the first S/H circuit 11 and the second S/H circuit 14 at the same time. The output of the second S/H circuit 14 is compared with the preset reference signal at the comparator 18, whereby a high level signal is sent to the clock pulse generator 19 when the output of the second S/H circuit 14 is higher than the preset reference signal. The reference signal is preset beforehand considering the maximum input level of the A/D converter 17. When the output signal of the comparator 18 is of a low level, the first analog switch 12 is opened and second analog switch 15 is closed to select the output of the second S/H circuit 14. When the output signal of the comparator 18 is of a high level, on the other hand, the first analog switch 12 is closed and the second analog switch 15 is opened to select the output of the first S/H circuit 11. That is, the signal passing through the second pre-amplifier 13 and amplified by the gain of sixty-four is selected when such high-gain amplified signal does not exceed the maximum input level of the A/D converter 17, and the signal passing through the first pre-amplifier 10 with the gain of unity is selected when the high-gain amplified signal may exceed the maximum input level of the A/D converter 17.

The selected signal is held again by the third S/H circuit 16, and the held signal is converted to digital data by the A/D converter 17. While the previously held signal is being A/D converted, the next sample holding is done at the next sampling point on the analog output signal of the detector by the first S/H circuit 11 and the second S/H circuit 14. From the clock pulse generator 19 to the microcomputer 20 is sent a gain signal GS representing which of the gain, unity or factor of sixty-four, is used before the signal is held by the third S/H circuit 16. When the gain signal GS tells that the analog signal is amplified by unity, the microcomputer 20 multiplies the converted data by sixty-four before storing it in the memory, and when the gain signal GS tells that the analog signal is amplified by a factor of sixty-four, the converted data is stored in the memory as it is.

In summary, when the analog output signal from the detector is small, it is amplified with a larger gain, and when the analog output signal from the detector is large, it is amplified with a smaller gain so that input to the A/D converter is adequately adjusted within its allowable range. Thus an analog output signal from the detector having a dynamic range larger than that of the A/D converter can be sampled and A/D converted.

The sampling section of the conventional signal processor described above is rather complicated and requires many constituents, so that it tends to be expensive. Another drawback is that it is vulnerable to external noises and is difficult to perform high-precision analysis because the analog signal passes two S/H circuits and the signal path is long. This necessitates a noise shield to the signal line, which also increases the cost.

SUMMARY OF THE INVENTION

One of the objectives of the present invention is therefore to provide a signal processor for a measurement apparatus or sample analyzer which has a large dynamic range and is highly impervious to external noises with a simple structure and low cost.

A signal processor for a measurement apparatus according to the present invention includes:

a) an amplifier for amplifying an analog signal output from the measurement apparatus with a variable gain;

b) an A/D converter for converting the amplified analog signal into a digital data;

c) a gain determining element for determining the gain of the amplifier based on the value of the digital data; and d) a data processor for producing a measurement data by processing a plurality of sequential digital data with a preset method taking account of the gain of the amplifier and the value of the digital data.

In the signal processor according to the present invention, the analog output signal of the measurement apparatus is first amplified by the amplifier, where the gain can be changed. The amplified analog signal is then sampled and converted by the A/D converter to a digital data. The gain determining element determines the gain of the amplifier based on the value of the digital data. Specifically, for example, when the value of the digital data is smaller than a preset reference value, the gain determining element determines the gain at a larger value, which will be used for the next sampled data. When, conversely, the value of the digital data is larger than another preset reference value, the gain determining element determines the gain at a smaller value so that a signal saturation in the A/D converter will be prevented in the next data sampling.

The data processor produces a measurement data from a plurality of sequentially sampled digital data with a preset method taking account of the gain of the amplifier and the value of the digital data. For example, when the value of one of a plurality of (two, for example) digital data is greater than the preset second reference value, i.e., when the input signal saturated (or may have saturated) in the A/D converting operation, the data is disregarded and the other data is used as the measurement data. This prevents producing an erroneous measurement data and assures the quality and preciseness of the sample analysis using the measurement data. When both data are usable, the average of the two is used as the measurement data. The data processor multiplies the digital data by an appropriate value based on the value of the gain of the amplifier so that the difference in the amplifying gain of the analog signal is cancelled.

Since the gain for amplifying the analog input signal is changed judging from the value of the digital data after the analog signal is A/D converted, the number of parts in the analog section is reduced compared to the conventional signal processor. Thus the construction of the analog section is simplified and the cost of the signal processor decreases. Another advantage of the signal processor of the present invention is that it is impervious to external noises because the length of line in the analog section becomes shorter. This brings about an enhanced S/N ratio of the signal processor and improves the precision of sample analysis by the measurement apparatus or sample analyzer.

DETAILED DESCRIPTION OF A PREFERRED EMBODIMENT

Figure 1:
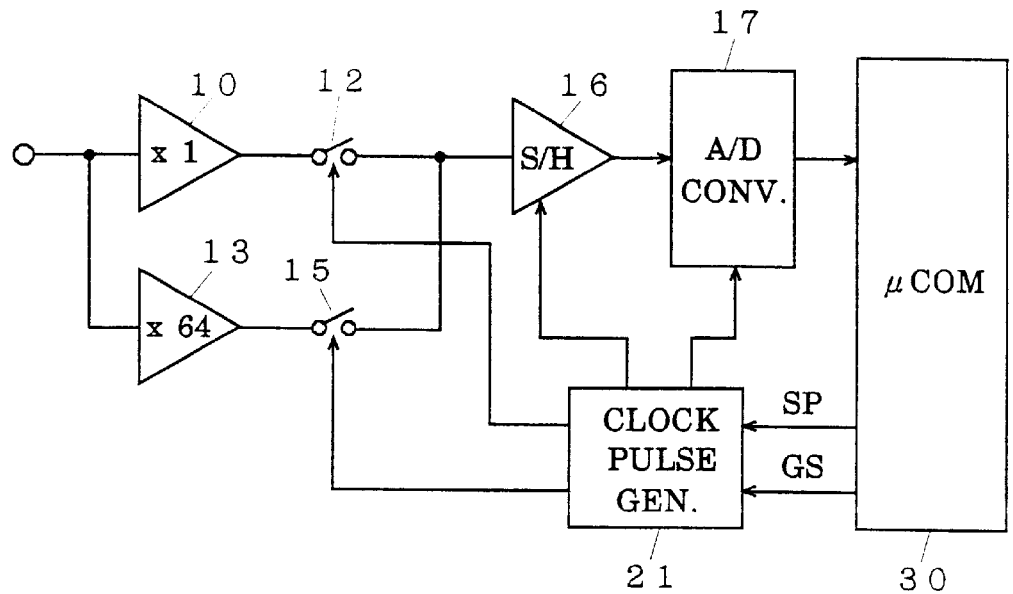
FIG. 1 is a block diagram of the data sampling section of a signal processor as an embodiment of the present invention.
Figure 5:
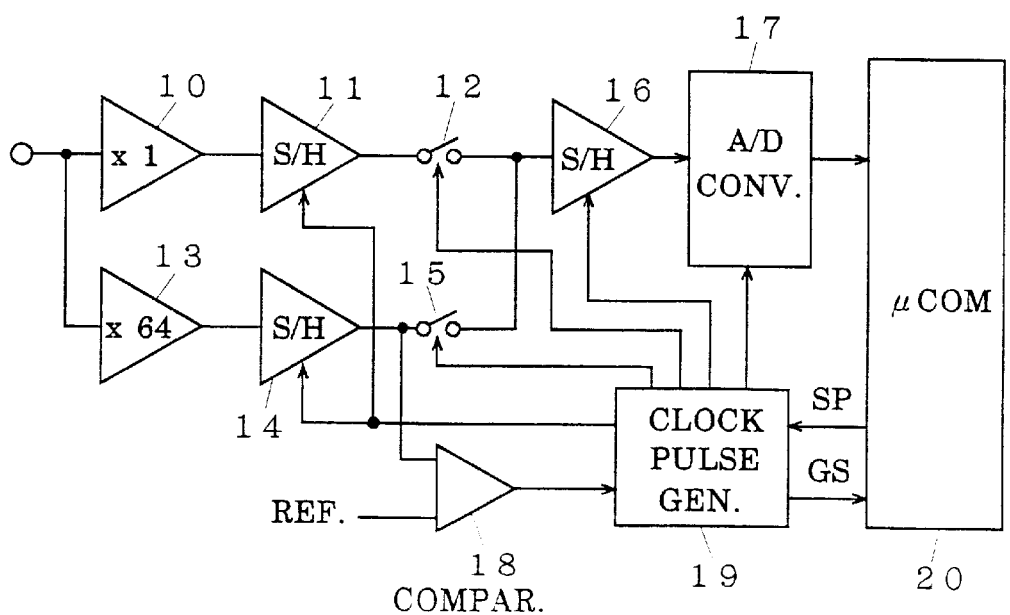
FIG. 5 is a block diagram of the data sampling section of a conventional signal processor.

FIG. 1 is a block diagram of the data sampling section of a signal processor embodying the present invention. In the data sampling section of the present embodiment, the first S/H circuit 11, the second S/H circuit 14 and the comparator 18 comprised in the same section of the conventional signal processor as in FIG. 5 are not necessary, but the microcomputer 30 is assigned with the following functions.

Figure 2:
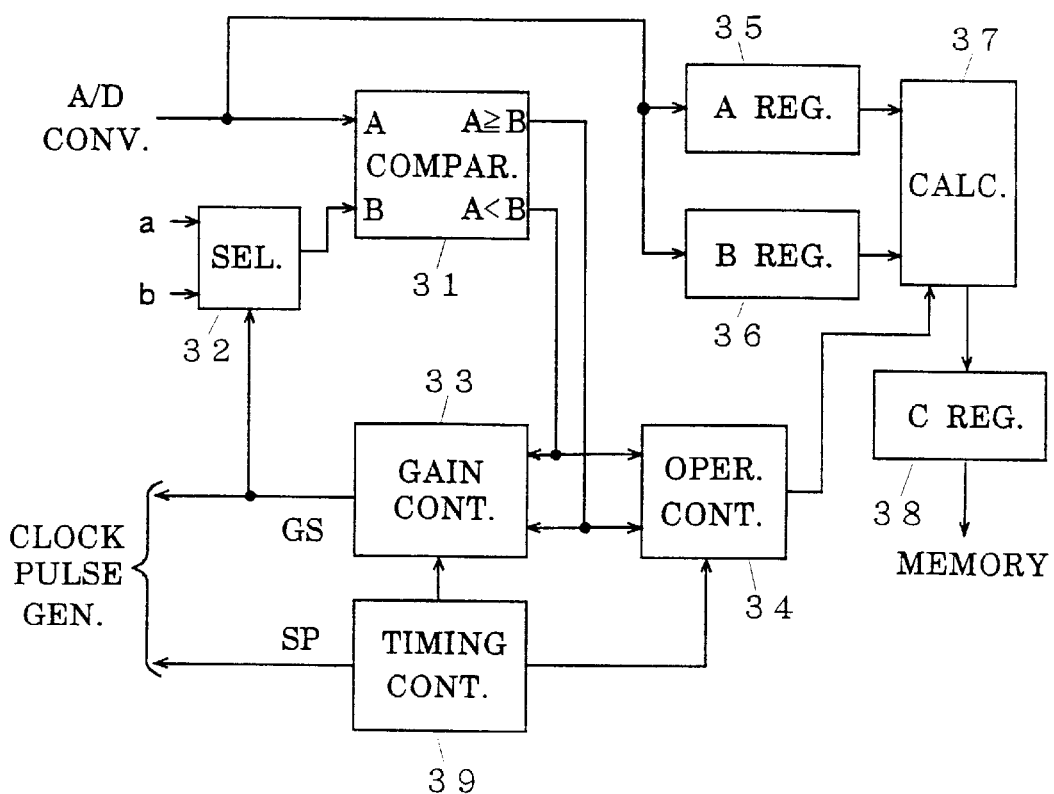
FIG. 2 is a functional block diagram of a portion of a microcomputer relating to the data sampling section.

FIG. 2 is a block diagram of functions performed by the microcomputer 30 in a data sampling operation. A comparing block (COMPAR.) 31, selecting block (SEL.) 32, gain control block (GAIN CONT.) 33 and operation control block (OPER. CONT.) 34 examine the value of a digital data and control the operation of these blocks based on the value. An A register block (A REG.) 35, B register block (B REG.) 36, calculating block (CALC.) 37 and C register block (C REG.) 38 process two consecutive A/D converted data to obtain a measurement data.

Figure 3:
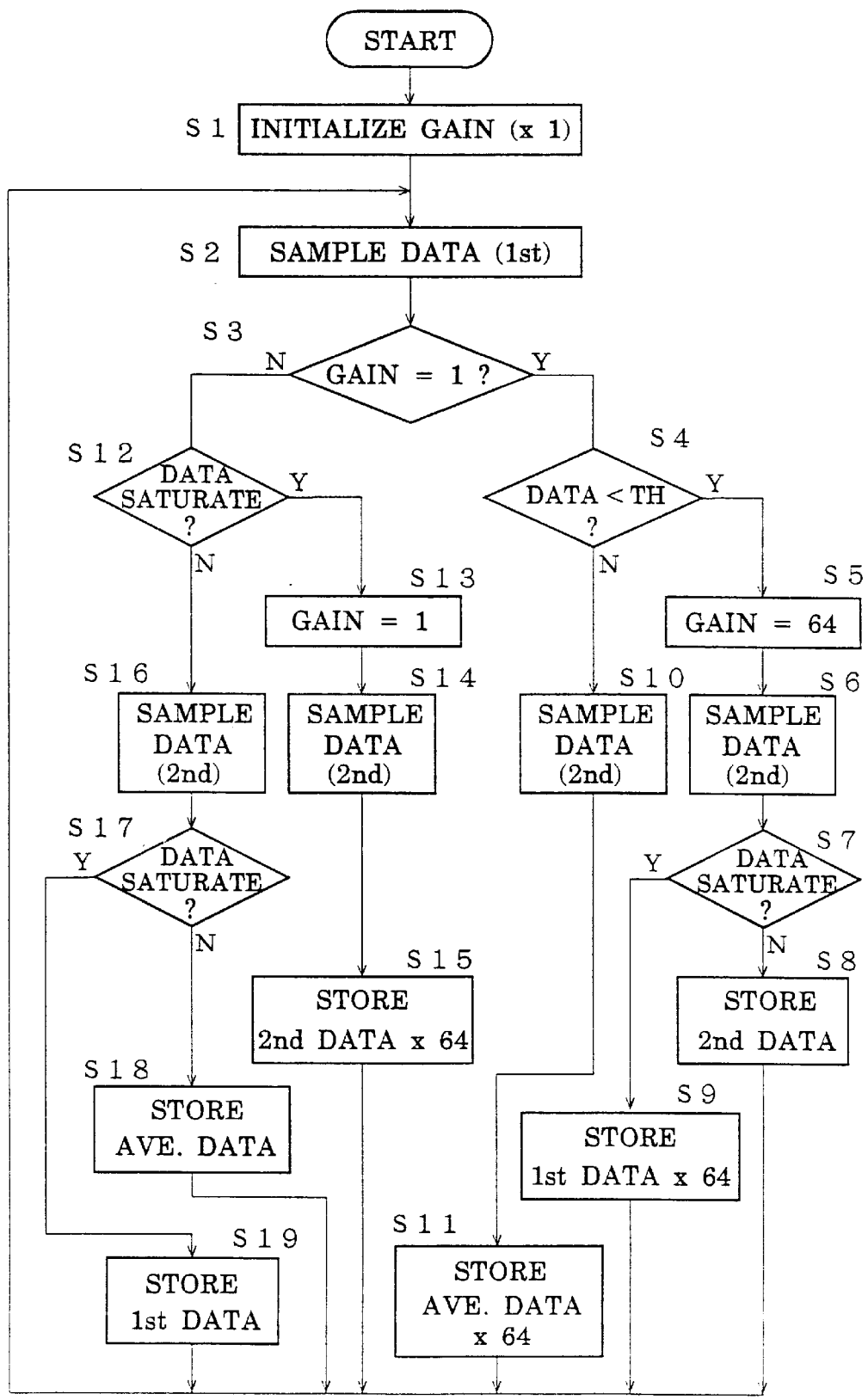
FIG. 3 is a flow chart of the data sampling operation of the embodiment.

The data sampling operation performed by the structure of FIGS. 1 and 2 is described referring to the flowchart of FIG. 3. First the clock pulse generator 21 closes the first analog switch 12 and opens the second analog switch 15 at step S1 to initialize the gain at unity. It is of course possible to initialize the gain at sixty-four (64) instead, in which case the first analog switch 12 is opened and the second analog switch 15 is closed.

After the initial gain is set at unity, the output signal of the first pre-amplifier 10 is held by the S/H circuit 16, and the held signal is converted to a digital data by the A/D converter 17. The digital data is sent to the microcomputer 30 at step S2, where the digital data as the first data is stored in the A register 35, and is also given to the comparing block 31. A data selected by the selecting block 32 is also given to the comparing block 31 as a reference.

When the gain is at unity, the process proceeds from step S3 to S4 where it is determined at the comparing block 31 whether the value of the digital data is smaller than a preset threshold value b. When the value of the digital data is larger than the threshold value b, the gain control block 33 outputs a gain signal GS to maintain the current gain of unity. Then the output signal of the first pre-amplifier 10 is held by the S/H circuit 16 and is converted to a digital data by the A/D converter 17 again (step S10). The digital data this time as the second data is stored in the B register 36. Since the first and second digital data samples are both from the detection signal amplified by the gain of unity, the calculating block 37 calculates, under the control of the operation control block 34, the average value of the data in the A register 35 and data in the B register 36, and then multiplies the average value by a factor of sixty-four to store the product in the C register 38 (step S11).

When the digital data is smaller than the threshold value b at step S4, the gain control block 33 outputs a gain signal GS to change the gain to a factor of sixty-four. Responsive to the gain signal GS, the clock pulse generator 21 opens the first analog switch 12 and closes the second analog switch 15, whereby a detection signal amplified by a factor of sixty-four at the second pre-amplifier 13 is provided to the S/H circuit 16 (step S5). The signal is held by the S/H circuit 16 and converted to a digital data by the A/D converter 17, which is stored in the B register 36 as the second data and is also given to the comparing block 31 (step S6).

Then it is judged at step S7 whether the digital data saturates in the A/D converting operation. Specifically, the selecting block 32 selects a preset reference value a and gives it to the comparing block 31. The value a is preset regarding the maximum input level of the A/D converter 17. It is preferable to set the value a somewhat smaller than that taking account of a noise allowance. When, therefore, the value of the sampled digital data is larger than the preset reference value a, it is assumed that the A/D converting operation is not done properly. Thus when the second sampled data is judged larger than the preset reference value a, the process proceeds from step S7 to step S9 whereby the calculating block 37 does not use the second sampled data but uses only the first sampled data stored in the A register 35. The first sampled data is multiplied by the factor sixty-four and stored in the C register 38. When the second sampled data is judged not larger than the preset reference value a at step S7, the calculating block 37 gives the second sampled data stored in the B register 36 to the C register 38 (step S8).

After storing a measurement data in the C register 38 by the operation of step S8, S9 or S11, the process returns to step S2 where the first data sampling is done to obtain the next measurement data. When the gain is set at sixty-four by the preceding operation (i.e., when the process returns from step S8 or S9 to step S2), the process proceeds from step S3 to step S12. In step S12, it is judged, similarly to step S7, whether the first sampled data saturates in the A/D converting operation. When it is judged affirmatively, the gain control block 33 sends out a gain signal GS to change the gain to unity. Responsive to the gain signal GS, the clock pulse generator 21 closes the first analog switch 12 and opens the second analog switch 15, whereby the analog output signal of the first pre-amplifier 10 is sent to the S/H circuit 16 (step S13). The signal is held by the S/H circuit 16 and converted to a digital data by the A/D converter 17. The sampled data is stored in the B register 36 as the second sampled data (step S14). The calculating block 37 does not use the first sampled data in this case because the first sampled data saturates in the A/D converting operation, but uses only the second sampled data stored in the B register 36. The second sampled data is multiplied by the factor sixty-four and stored in the C register (step S15).

When it is judged at step S12 that the first sampled data does not saturate, the gain control block 33 sends out a gain signal GS for maintaining the gain at a factor of sixty-four. Then the output of the second pre-amplifier 13 is held by the S/H circuit 16 and converted to a digital data by the A/D converter 17 (step S16). The digital data is stored in the B register 36 as the second sampled data and also given to the comparing block 31. It is judged at step S17 whether the second sampled data saturates, similarly to step S7. When it is judged affirmatively, the calculating block 37 gives the first sampled data stored in the A register 35 to the C register 38 (step S19). When the second sampled data is judged not to saturate, the calculating block 37 calculates the average of the first sampled data stored in the A register 35 and the second sampled data stored in the B register 36, and stores the average data to the C register 38 (step S18).

The data temporarily stored in the C register 38 by the operation of step S8, S9, S11, S15, S18 or S19 is read out before the next measurement data is stored in the C register 38 and securely stored in a measurement data memory (not shown).

Figure 4:
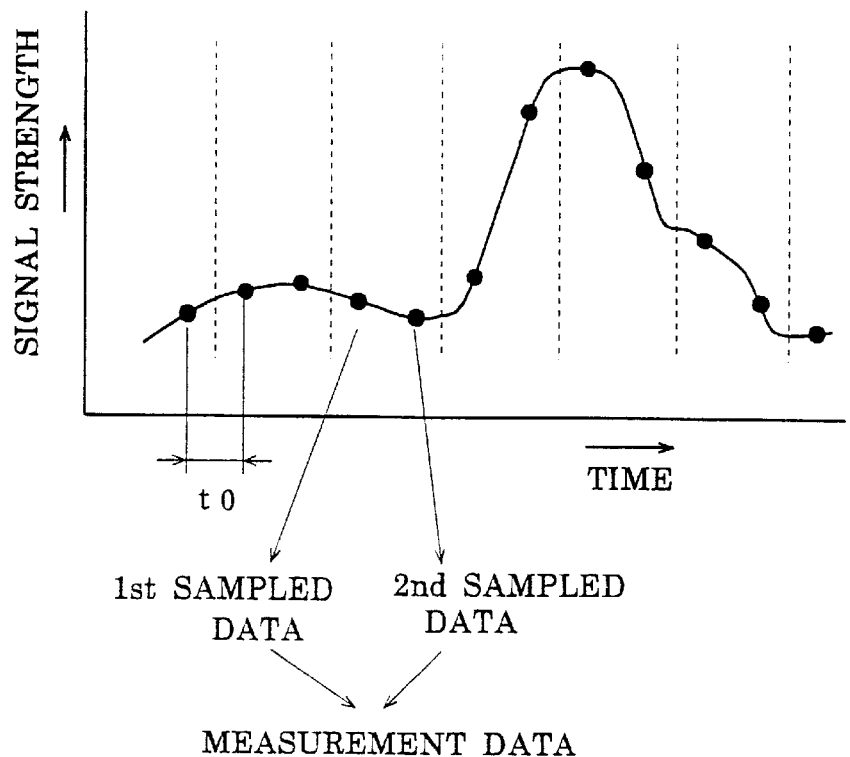
FIG. 4 is a graph showing an analog signal wave and data sampling points on the wave.

FIG. 4 shows an example of the analog output signal of a sample analyzer and the sampling points on the signal wave. The timing of the sampling is controlled by the timing control block (TIMING CONT.) 39 of the microcomputer 30. Normally, data are sampled at a fixed interval of $t_0$ and the first and the second sampled data are used to obtain a measured data as described above. Since the values of data derived from adjacent points on a signal wave are closely correlated to each other, the gains for the first sampling point and that for the second, and that for the second and that for the next are almost the same except at an abnormally turbulent part of the signal wave.

The sampling speed of the present signal processor should be twice as great as that for a traditional signal processor since, as described above, two sampling operations should be done to obtain a measurement data. Such increase in the sampling speed, though, is not actually disadvantageous in a signal processor for a measurement apparatus or sample analyzer such as a GC/MS. In a GC/MS, the output signal of the detector is generated while a preset range of mass/charge (m/z) ratio is scanned, and a mass spectrum with the m/z ratio as the abscissa and the strength of the detection signal as the ordinate is obtained. The scanning speed of the m/z ratio is normally changeable. However, changing the sampling speed in the sampling section along with the scanning speed is rather difficult because it makes the hardware rather complicated. Conventionally, in such cases, the sampling speed is fixed and the number of sampling times at one point is changed according to the scanning speed. That is, the sampling speed is set adequately higher than the speed necessary when the scanning speed is at an average, and when the scanning speed is increased, the number of sampling times at a point is decreased. The number of sampling times at a point is increased, on the other hand, when the scanning speed is decreased. Since such a method that a point is sampled a plurality of times as described above is conventionally used, it can be applied to the signal processor of the present embodiment, whereby it is not necessary to use a specially constructed high-speed S/H circuit or A/D converter.

Obviously, many modifications and variations of the present invention are possible in light of the above teachings. It is therefore to be understood that within the scope of the appended claims, the invention may be practiced other than as specifically described. For example, the gain is changed between two values that are unity and a factor of sixty-four in the above description. More grades can be provided for the gain, as unity, factors of sixteen (16) and two hundred and fifty-six (256). More than three sampled data can be used, instead of two as in the above description, to produce a measurement data.

For changing the gain, distinct sets of pre-amplifiers and analog switches are used in the above description. It is possible to use a single amplifier, instead of two, whose gain is externally controllable.

In the case of a signal processor for a GC/MS, gain signals GS can be stored in a memory while a preset range of m/z ratio is scanned for a sample. The gain signals GS may be used, or referred to at least, afterwards when the same or similar sample is analyzed by the GC/MS.

What is claimed is:

1. A signal processor for a measurement apparatus comprising:
   a) an amplifier for amplifying an analog signal output from the measurement apparatus with a variable gain;
   b) an A/D converter for converting the amplified analog signal into a digital data set;
   c) gain determining means for determining the gain of the amplifier based on the digital data set;
   d) digital storing means for storing a plurality of digital data sets sequentially output from the A/D converter; and
   e) data processing means for producing one measurement data set by processing the plurality of digital data sets stored by the data storing means with a preset method taking account of the gain of the amplifier and the value of each digital data set.

2. The signal processor according to claim 1, where the signal processor further comprises gain compensating means for compensating the difference in the gain with which the analog output signal is amplified by multiplying the value of a corresponding digital data set by a value corresponding to the value of the gain.

3. The signal processor according to claim 1, where the gain determining means determines the gain at a smaller value when a value of the digital data set is larger than a preset reference value, and determines the gain at a larger value when the value of the digital data set is smaller than another preset reference value.

4. The signal processor according to claim 1, where the data processing means disregards a digital data set among the plurality of digital data sets whose value is larger than a preset reference value in producing the measurement data.

5. The signal processor according to claim 1, where the amplifier is composed of a plurality of unit amplifiers each having a fixed value of gain, and the gain of the amplifier is changed by selecting one of the plurality of unit amplifiers.

* * * * *